United States Patent [19]

Bosshold

[11] 4,085,750
[45] Apr. 25, 1978

[54] EYEDROPPER BOTTLE ATTACHMENT

[76] Inventor: Barry L. Bosshold, 1005 J St., #366, Davis, Calif. 95616

[21] Appl. No.: 556,739

[22] Filed: Mar. 10, 1975

[51] Int. Cl.² ............................................. A61M 31/00
[52] U.S. Cl. ...................................... 128/233; 128/249
[58] Field of Search ................ 222/192; 128/233, 249, 128/244, 242, 345, 20, 17

[56] References Cited

U.S. PATENT DOCUMENTS

| | | | |
|---|---|---|---|
| 2,898,911 | 8/1959 | Taylor | 128/249 |
| 3,058,466 | 10/1962 | Routsong | 128/233 |
| 3,314,426 | 4/1967 | Carroll | 128/249 X |
| 3,776,226 | 12/1973 | Triplett | 128/345 X |
| 3,841,318 | 10/1974 | Olson | 128/20 |
| 3,872,866 | 3/1975 | Lelicoff | 222/192 X |

FOREIGN PATENT DOCUMENTS 1,025,304   1/1953   France .................................. 128/233

OTHER PUBLICATIONS

George Tiemann & Co.'s Surgical Instruments, 1889 Catalog, "Opthalmic", p. 151.

Primary Examiner—Allen N. Knowles
Assistant Examiner—Francis J. Bartuska
Attorney, Agent, or Firm—Melvin R. Stidham

[57] ABSTRACT

An eyedrop bottle attachment has a pair of flexible arms which, in use, extend upwardly therefrom. The arms are squeezed together somewhat, and pads on the ends of the arms are pressed gently against the closed eyelids so that when released, the arms flex back to force the eyelids apart. Thereafter, the pads hold the eye open and provide a steady support for the bottle to insure accurate placement of the drops.

9 Claims, 10 Drawing Figures

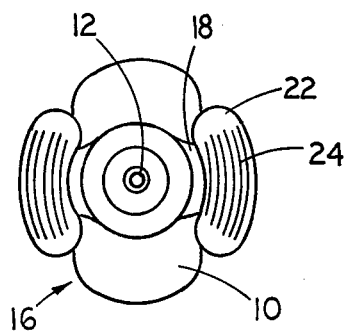
FIG.-3-
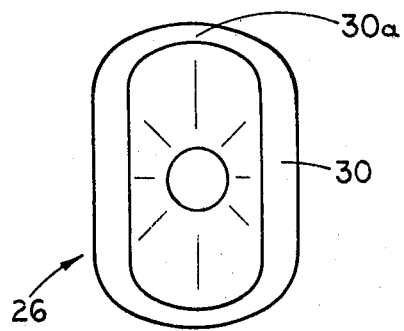
FIG.-6-
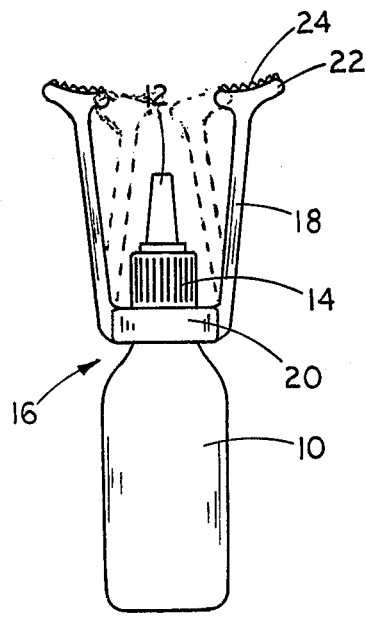
FIG.-2-
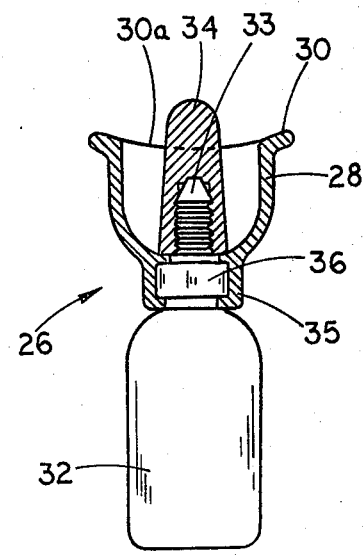
FIG.-5-
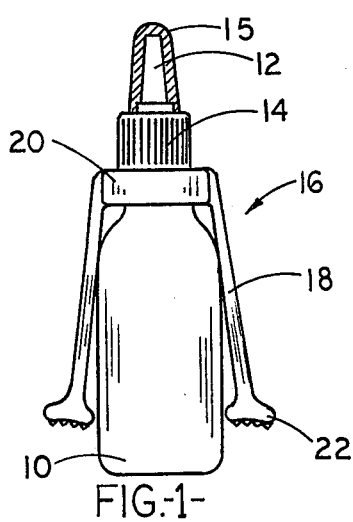
FIG.-1-
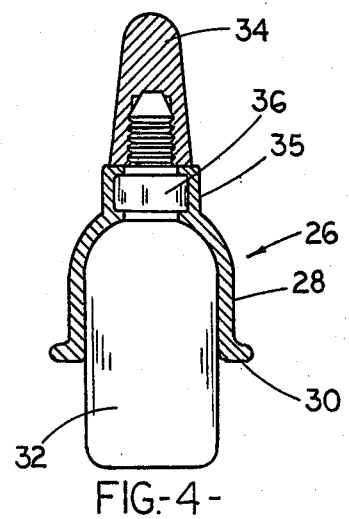
FIG.-4-

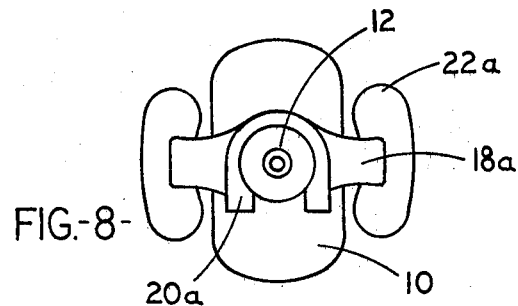
FIG.-8-
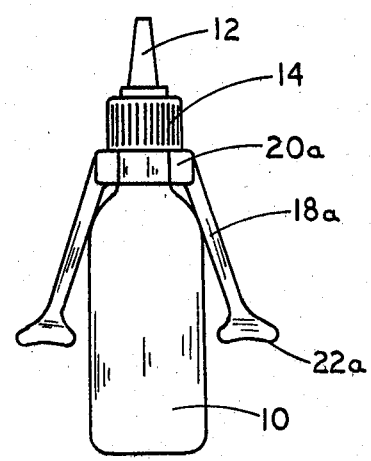
FIG.-7-
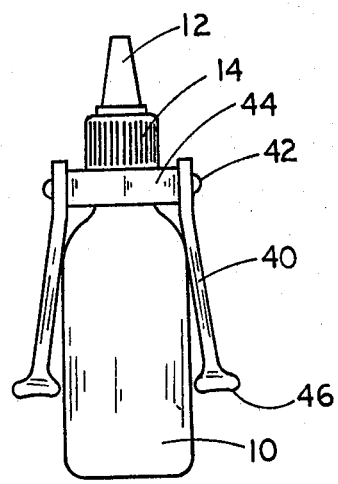
FIG.-9-
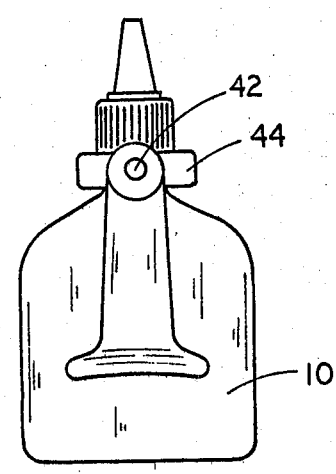
FIG-10-

EYEDROPPER BOTTLE ATTACHMENT

BACKGROUND OF THE INVENTION

Medication and cleansing fluids are commonly available in bottles, often of the squeeze type, with a small nozzle through which drops may be applied directly to the eye. As is well known, considerable difficulty is often experienced in keeping the eye open and steadying the hand simultaneously for a period of time sufficient to insure accurate placement of the drops. One attempt to overcome this difficulty was found in a spray attachment which ejects a liquid in the form of a mist sprayed from within a cup placed over the eye. However, such a spray could carry with it dust particles or other foreign materials which may have settled on the surface of the cup when not in use.

OBJECTS OF THE INVENTION

It is an object of this invention to provide an attachment for an eyedropper bottle which holds the eyelids open while the drops are being applied.

It is a further object of this invention to provide an attachment for an eyedropper bottle which provides a support out of direct contact with the eye itself for steadying the bottle.

It is a further object of this invention to provide an eyedropper attachment which supports the bottle during use, out of the path of the liquid being directed into the eye.

Other objects and advantages of this invention will become apparent from the description to follow when read in conjunction with the accompanying drawings.

BRIEF SUMMARY OF THE INVENTION

In carrying out this invention, I provide a pair of flexible arms which, in use, extend upwardly from the neck area of an eyedropper bottle. The arms have sufficient flexural strength to return to normal configuration after being flexed. Carried on the ends of the arms are pads or flat supports which may be lightly pressed against the eyelids without discomfort. Hence, the arms function as a support to locate the nozzle of the eyedropper bottle directly over the eye. In addition, the arms may function to open the eye and hold it open during use. Specifically, the arms are squeezed toward each other by grasping them around their outer surfaces and the pads are pressed lightly against the closed or partially closed eyelids. Then, when released the flexural strength of the arms will force the eyelids apart, locating the nozzle of the eyedropper bottle directly over the open eye. The arms provide a steadying support for the bottle while the drops are being applied. The arms may be carried on a collar supported around the neck of the bottle whereby when inverted, they will hang down alongside the bottle for convenience in storing and carrying. In addition, as so disposed they will not interfere with normal use of the eyedropper. In one form of the bottle, the arms are formed by the opposite sides of the more or less oval cup. In this form, the other sides of the cup are deformed when the cup is squeezed and aid in restoring the cup to its normal configuration when released.

BRIEF DESCRIPTION OF THE DRAWINGS

In the drawings:

FIG. 1 is a side view of one embodiment of the attachment as position when not in use;

FIG. 2 is a side view of the embodiment of FIG. 1 in position for use;

FIG. 3 is a top view of the embodiment of FIG. 1;

FIG. 4 is a side view, partially in section of another embodiment of this invention;

FIG. 5 is a side view partially in section of the embodiment of FIG. 4 in position for use;

FIG. 6 is a top view of the embodiment of FIG. 4;

FIG. 7 is a side view of a third embodiment of this invention;

FIG. 8 is a top view of the embodiment of FIG. 7;

FIG. 9 is a side view of still another embodiment of this invention; and

FIG. 10 is a front view of the embodiment of FIG. 9.

DESCRIPTION OF PREFERRED EMBODIMENT

The Embodiment of FIGS. 1 to 3

Referring now to FIGS. 1 to 3 with greater particularity, there is shown a bottle 10 which may be of the plastic squeeze type adapted to contain a quantity of fluid medication or cleanser to be applied to the human eye by projection of the substance through a suitable nozzle 12 carried on the bottle top 14.

The eyedropper attachment 16 of this invention includes a pair of flexible arms or wings 18 which may be carried on an integral collar 20 adapted to be carried around the neck of the bottle 10. When the attachment 16 is not in use, the collar 20 may be inverted to the position shown in FIG. 1 and a cap 15 placed over the nozzle 12. With the collar 20 so inverted, the arms depend along the front and back sides of the bottle 10 to facilitate storage or carrying the bottle in one's purse or pocket. As so positioned the arms will not impede conventional use of the eye dropper. When in use, the cap 14 may be removed and the collar reversed to the position shown in FIG. 2 wherein the arms extend upward from the neck of the bottle 10. Carried on the ends of the arms are suitable pads 22 which are adapted to be placed against the eyelids to hold the eyelids apart and support the bottle 10 while the medicine or soothing agent is applied to the eye. If desired, the surfaces of the pads may be gently ridged or knurled at 24 to aid in gripping the eyelids, particularly if wet.

In operation, the arms 18 are placed in their upraised position of FIG. 2 to be used as a support for the bottle as the drops are being placed. If desired, in fact, the arms may first be squeezed together slightly, as shown by the dotted lines, and the pads 22 placed directly and gently against the closed eyelids. Then, the arms 18 may be released to allow the flexural strength of the arms 18 to restore them outward to their normal dispositions and force the eyelids apart prior to application of the eye drops. Continued light pressure of the pads 22 against the eyelids holds the eye open and steadies the bottle 10.

The Embodiment of FIGS. 4 to 6

Referring now to FIGS. 4 to 6, the attachment 26 may take the form of a cup 28 having smoothly curved outer rims 30, the opposite portions of which function as the eyelid pads. In operation, the opposite sides 28 are squeezed together as in the configuration of FIG. 1 whereby, when released, they would naturally spring apart to force the eyelids open. With the eyelids open the cup 28 performs the additional function of shielding the eye from light to which some may be sensitive. If desired, the short opposite sides may be formed with relatively thin outer lips 30a to facilitate bending thereof. In any event the restoring forces of the material completely around the cup aid in restoring the opposite sides 28. With the cup 28 in the position shown in FIG. 5, the nozzle 33 is disposed well below the level of the lips or pads 30, 30a to protect it against contamination. In addition, a cap 34 is made sufficiently tall that it may be grasped without touching the inner surfaces of the cup 26 or the nozzle tip 33.

When not in use, the cup 26 may be inverted whereby it will surround the sides of the bottle 32 as shown in FIG. 4. Whether inverted or upright for application of drops, the cup 26 may be held in place by snap fit of an annular collar 34 thereon around an enlarged portion 36 surrounding the neck of the bottle.

The Embodiment of FIGS. 7 and 8

The embodiment of FIGS. 7 and 8 is similar to that of FIGS. 1 to 3 except that the collar 20 is replaced by a U-shaped clamp 20a which engages around the neck of the bottle 10 whether inverted, as shown, or upraised for operation. The arms 18a and pads 22a are formed and function as do the corresponding components of FIG. 1.

The Embodiment of FIGS. 9 and 10

Referring now to FIGS. 9 and 10, the arms 40 may be pivotally mounted at 42 on a supporting collar 44 carried on the neck of the bottle 10. Hence, the arms may be pivoted between the retracted positions shown, to an upraised position with pads 46 extended for application of drops, without requiring removal of the collar from the bottle 10.

While this invention has been described in conjunction with preferred embodiments thereof, it is obvious that modifications and changes therein may be made by those skilled in the art without departing from the spirit and scope of this invention as by defined by the claims appended hereto.

What is claimed as invention is:

1. An attachment for a lightweight squeeze type eyedropper bottle comprising:
   a pair of arms:
   pads on the ends of said arms adapted to be placed against the outer surfaces of the eyelids;
   frictional surfaces on said pads;
   means for supporting said arms around and near the top of said eyedropper bottle to extend upwardly therefrom with said pads on opposide sides of the nozzle thereof spaced normally to be accommodated within the eye socket so as to rest against the upper and lower eyelids when open;
   said arms being flexible so that same may be grasped and said pads moved closer together before being placed against the eyelids and having sufficient flexural strength when thereafter released to force the eyelids apart and enable movement of the fingers to the sides of the bottle for placement of drops;
   said supporting means enabling said arms to be inverted;
   said arms being so spaced relative to the size and shape of said eyedropper bottle that when inverted they depend closely along the sides of said eyedropper bottle.

2. The attachment defined by claim 1 wherein:
   said supporting means comprises a reversible collar adapted to fit around the neck of said bottle;
   said arms being carried on said collar.

3. The attachment defined by claim 1 wherein:
   said arms form opposite sides of a flexible cup; and the flexural strength restoring said opposite sides is asserted completely around the cup.

4. The attachment defined by claim 1 wherein:
   said supporting means comprises a clamp member adapted to engage around the neck of said bottle.

5. The attachment defined by claim 1 wherein:
   said supporting means engages around the neck of said bottle and including:
   pivot means securing said arms to said supporting for pivotal movement thereof between said extended position and said inverted position.

6. The attachment defined by claim 1 wherein:
   the surfaces of said pads are roughened for increased friction.

7. The attachment defined by claim 1 including:
   an enlarged portion around the neck of the bottle;
   a collar on which said arms are carried;
   said collar being engageable in a snap fit over and around said enlarged portion.

8. An attachment for a lightweight squeeze type eyedropper bottle comprising;
   a flexible cup;
   pads on opposite rims of said cup being spaced to engage against the outer surfaces of the eyelids for frictional engagement thereof;
   means for securing said cup near the top of said eyedropper bottle to extend upwardly therefrom;
   the flexibility of said cup enabling said opposite rims to be grasped and forced closer together before being placed against the eyelids but asserting flexural strength around the cup to restore it to normal configuration and force the eyelids apart.

9. The attachment defined by claim 8 including:
   an enlarged portion around the neck of the bottle;
   a collar on the base of said cup;
   said collar being engageable in a snap fit over and around said enlarged portion;
   said collar enabling said cup to be inverted to closely embrace said bottle.

* * * * *